(12) United States Patent
Voegele et al.

(10) Patent No.: US 9,877,782 B2
(45) Date of Patent: Jan. 30, 2018

(54) ELECTROSURGICAL INSTRUMENT END EFFECTOR WITH COMPLIANT ELECTRODE

(71) Applicant: Ethicon Endo-Surgery, Inc., Cincinnati, OH (US)

(72) Inventors: Aaron C. Voegele, Loveland, OH (US); Paul T. Franer, Cincinnati, OH (US); Geoffrey S. Strobl, Williamsburg, OH (US); Catherine A. Corbett, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 377 days.

(21) Appl. No.: 13/804,963

(22) Filed: Mar. 14, 2013

(65) Prior Publication Data
US 2014/0276731 A1 Sep. 18, 2014

(51) Int. Cl.
*A61B 18/18* (2006.01)
*A61B 18/14* (2006.01)
(Continued)

(52) U.S. Cl.
CPC .......... *A61B 18/18* (2013.01); *A61B 18/1442* (2013.01); *A61B 18/1445* (2013.01); *A61B 18/1447* (2013.01); *A61B 2017/00862* (2013.01); *A61B 2018/00059* (2013.01); *A61B 2018/0063* (2013.01); *A61B 2018/00607* (2013.01); *A61B 2018/1455* (2013.01)

(58) Field of Classification Search
CPC . A61B 18/1445; A61B 18/1442; A61B 18/14; A61B 18/18; A61B 18/1447; A61B 2017/00862; A61B 2018/00059; A61B 2018/00607; A61B 2018/0063; A61B 2018/1455
See application file for complete search history.

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

| WO | WO 99/40861 A1 | 8/1999 |
| WO | WO 99/40862 | 8/1999 |

OTHER PUBLICATIONS

U.S. Appl. No. 61/410,603, filed Nov. 5, 2010.
(Continued)

*Primary Examiner* — Lindsey G Wehrheim
(74) *Attorney, Agent, or Firm* — Frost Brown Todd LLC

(57) ABSTRACT

An end effector for operating on tissue comprises an upper jaw, a lower jaw, a flexible member, and a pair of conductive members. The upper jaw and the lower jaw are configured to receive tissue when in an open position and the upper jaw is movable toward the lower jaw. The flexible member is coupled to either the upper jaw or the lower jaw, and is configured to deform in response to compression of tissue between the jaws. One of the conductive members is associated with the flexible member and is configured to move with the flexible member in response to compression of tissue between the jaws. The end effector may be configured to manipulate the position of muscle within tissue in response to compression of tissue between the jaws.

16 Claims, 19 Drawing Sheets

(51) Int. Cl.
  *A61B 17/00*  (2006.01)
  *A61B 18/00*  (2006.01)

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,814,055 A | 9/1998 | Knodel et al. |
| 6,083,223 A * | 7/2000 | Baker ............... A61B 18/1445 606/49 |
| 6,500,176 B1 | 12/2002 | Truckai et al. |
| 6,783,524 B2 | 8/2004 | Anderson et al. |
| 6,978,921 B2 | 12/2005 | Shelton, IV et al. |
| 7,000,818 B2 | 2/2006 | Shelton, IV et al. |
| 7,112,201 B2 | 9/2006 | Truckai et al. |
| 7,125,409 B2 | 10/2006 | Truckai et al. |
| 7,143,923 B2 | 12/2006 | Shelton, IV et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,303,108 B2 | 12/2007 | Shelton, IV et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 7,918,848 B2 | 4/2011 | Lau et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 2005/0010211 A1* | 1/2005 | Suzuki ............... A61B 18/1445 606/45 |
| 2006/0079874 A1 | 4/2006 | Faller et al. |
| 2006/0217697 A1* | 9/2006 | Lau et al. ................ 606/29 |
| 2007/0191713 A1 | 8/2007 | Eichmann et al. |
| 2007/0282333 A1 | 12/2007 | Fortson et al. |
| 2008/0071268 A1* | 3/2008 | Hafner ............... 606/48 |
| 2008/0200940 A1 | 8/2008 | Eichmann et al. |
| 2009/0062795 A1* | 3/2009 | Vakharia et al. ........... 606/52 |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116379 A1 | 5/2012 | Yates et al. |
| 2013/0014375 A1* | 1/2013 | Hempstead et al. ........... 29/458 |
| 2013/0023868 A1 | 1/2013 | Worrell et al. |
| 2013/0030428 A1 | 1/2013 | Worrell et al. |
| 2013/0035687 A1 | 2/2013 | Hiller et al. |

OTHER PUBLICATIONS

U.S. Appl. No. 61/550,768, filed Oct. 24, 2011.
International Search Report and Written Opinion dated Sep. 15, 2014 for Application No. PCT/US2014/016893.

* cited by examiner

ELECTROSURGICAL INSTRUMENT END EFFECTOR WITH COMPLIANT ELECTRODE

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; U.S. Pub. No. 2012/0083783, entitled "Surgical Instrument with Jaw Member," published Apr. 5, 2012, now U.S. Pat. No. 8,888,809, issued on Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued on Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
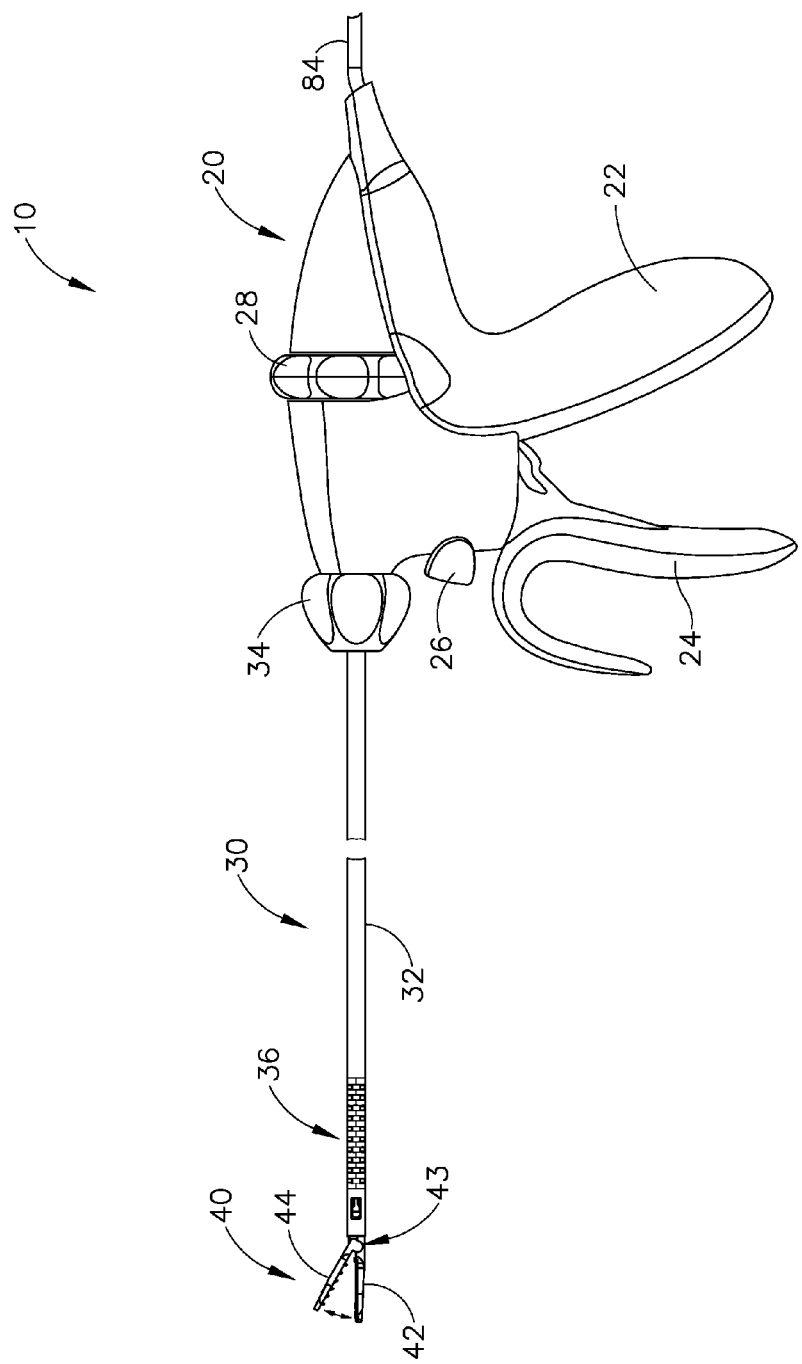
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, now U.S. Pat. No. 8,939,974, issued Jan. 27, 2015; U.S. Pub. No. 2012/0083783, now U.S. Pat. No. 8,888,809, issued Nov. 18, 2014; U.S. Pub. No. 2012/0116379, now U.S. Pat. No. 9,161,803, issued Oct. 20, 2015; U.S. Pub. No. 2012/0078243; U.S. Pub. No. 2012/0078247, now U.S. Pat. No. 9,402,682, issued Aug. 2, 2016; U.S. Pub. No. 2013/0030428, now U.S. Pat. No. 9,089,327, issued on Jul. 28, 2015; and/or U.S. Pub. No. 2013/0023868, now U.S. Pat. No. 9,545,253, issued Jan. 17, 2017. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button

(26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued on Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued on Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, now U.S. Pat. No. 9,545,253, issued on Jan. 17, 2017, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
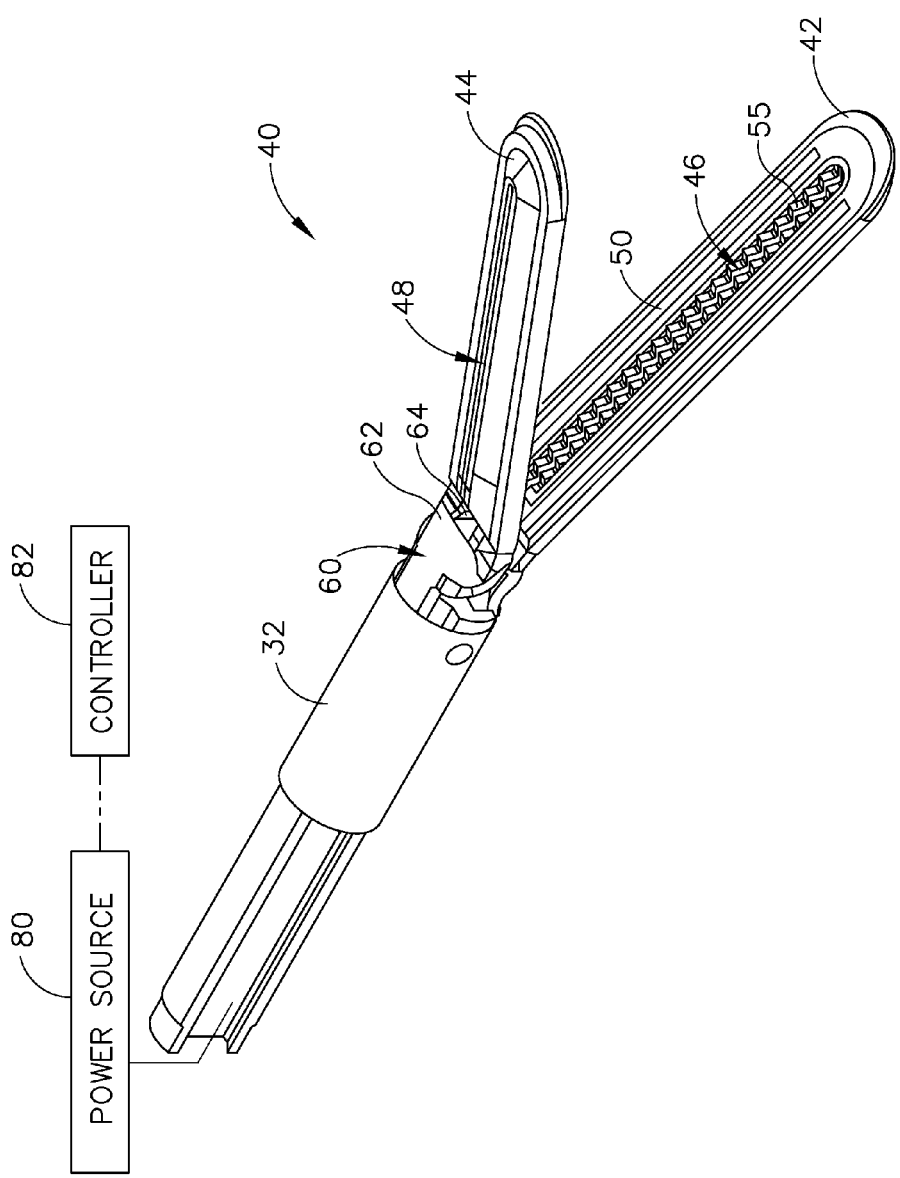
FIG. 2 depicts a perspective view of the end effector of the instrument of FIG. 1, in an open configuration.
Figure 3:
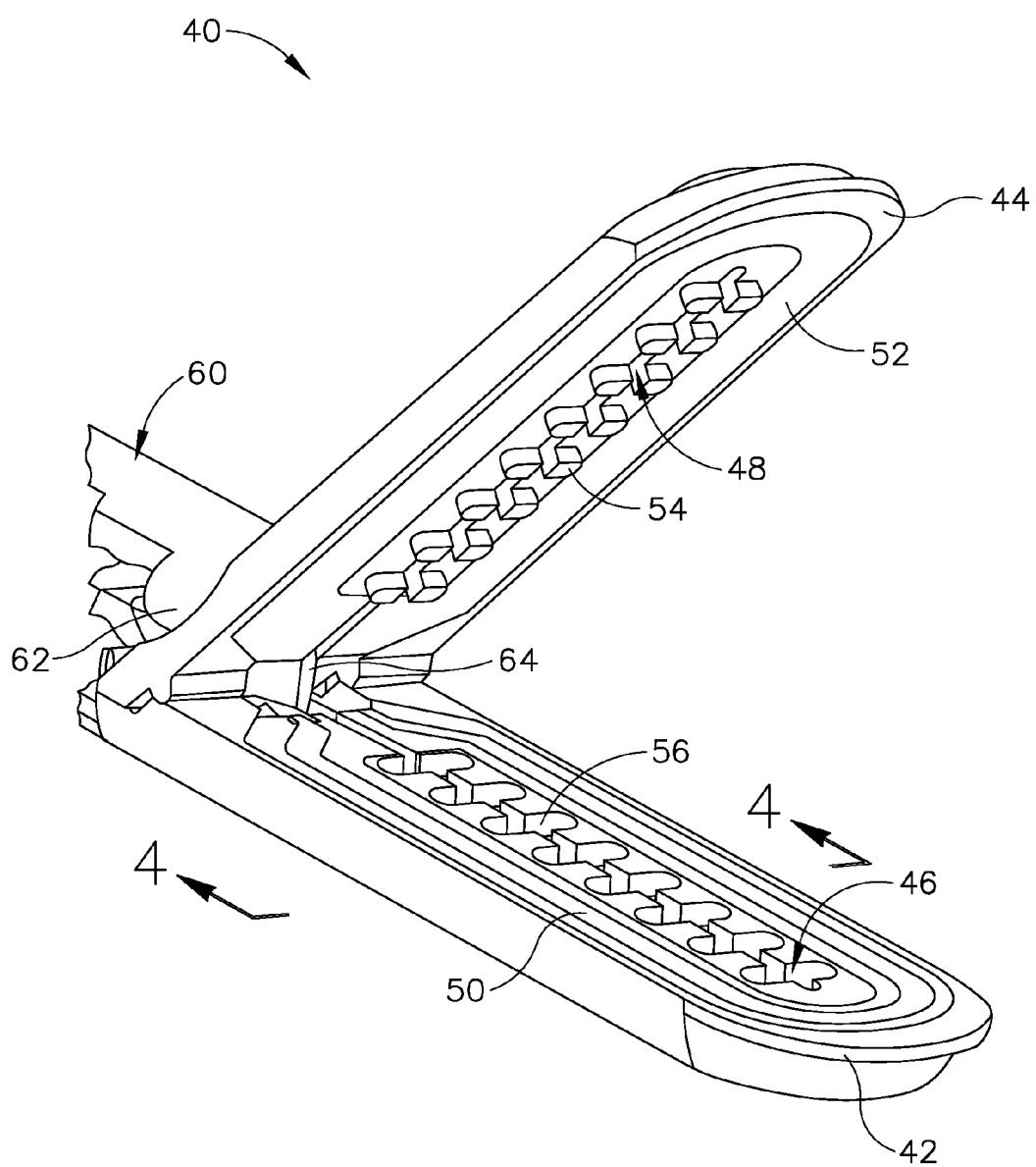
FIG. 3 depicts another perspective view of the end effector of the instrument of FIG. 1, in an open configuration.
Figure 4:
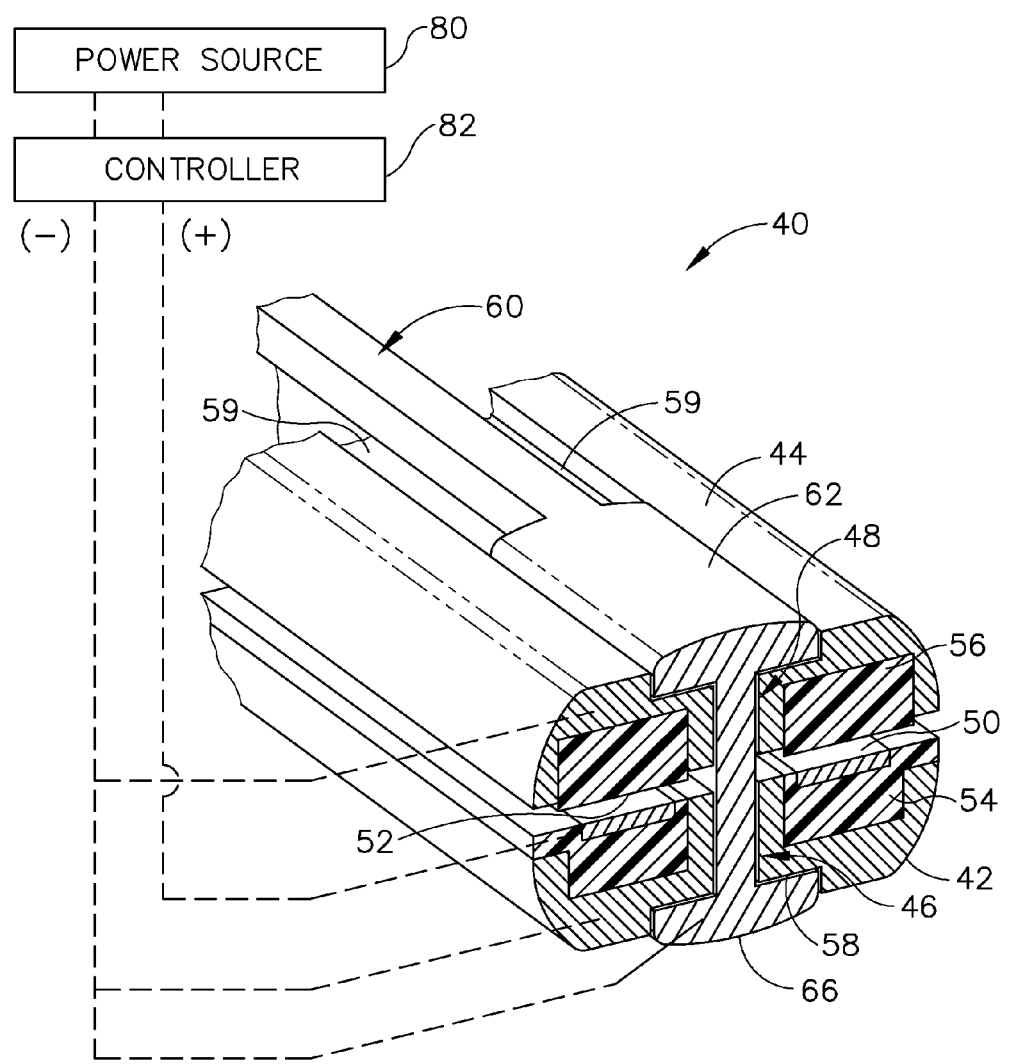
FIG. 4 depicts a cross-sectional end view of the end effector of FIG. 2, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued on May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued on Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued on Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
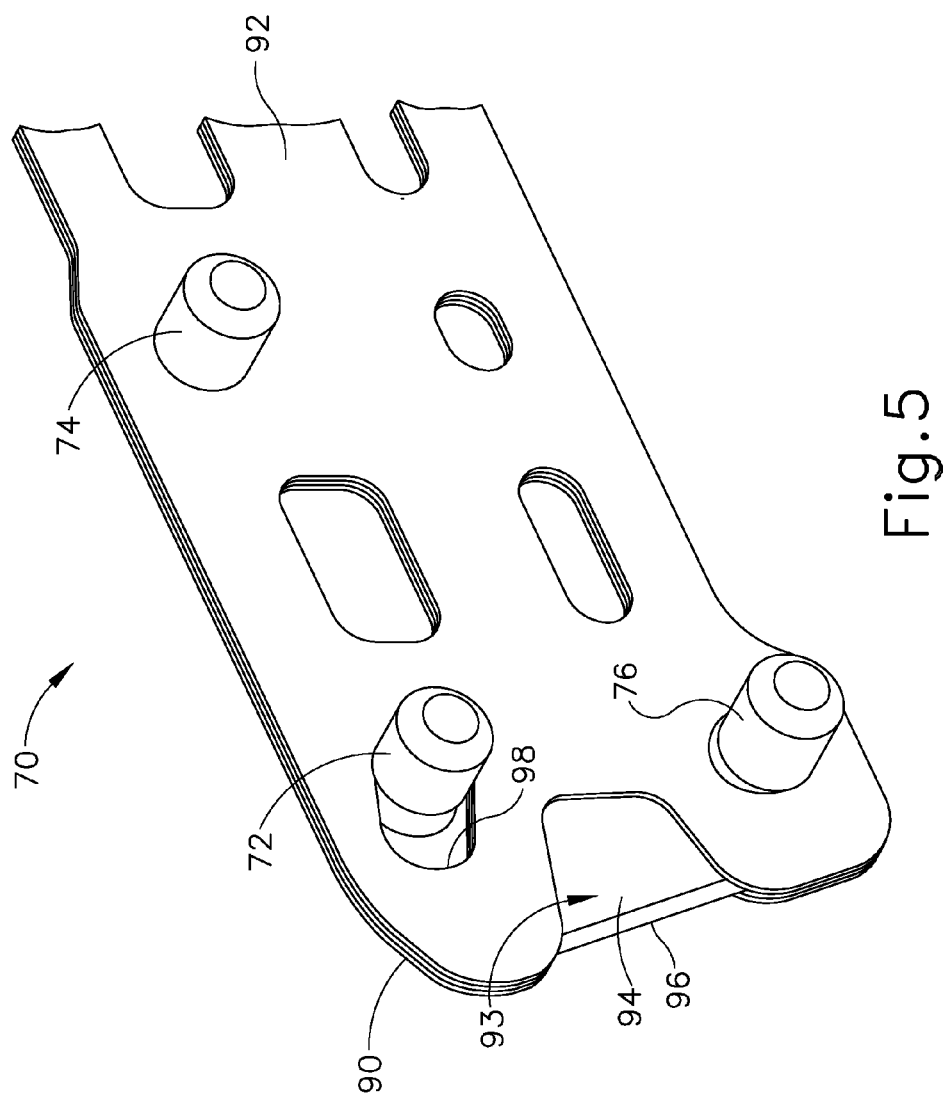
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Of course, firing beam (70) may have any other suitable configuration. By way of example only, firing beam (70) may be configured in accordance with at least some of the teachings of U.S. Pub. No. 2012/0083783, now U.S. Pat. No. 8,888, 809, issued Nov. 18, 2014, the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Alternative End Effector

Figure 6:
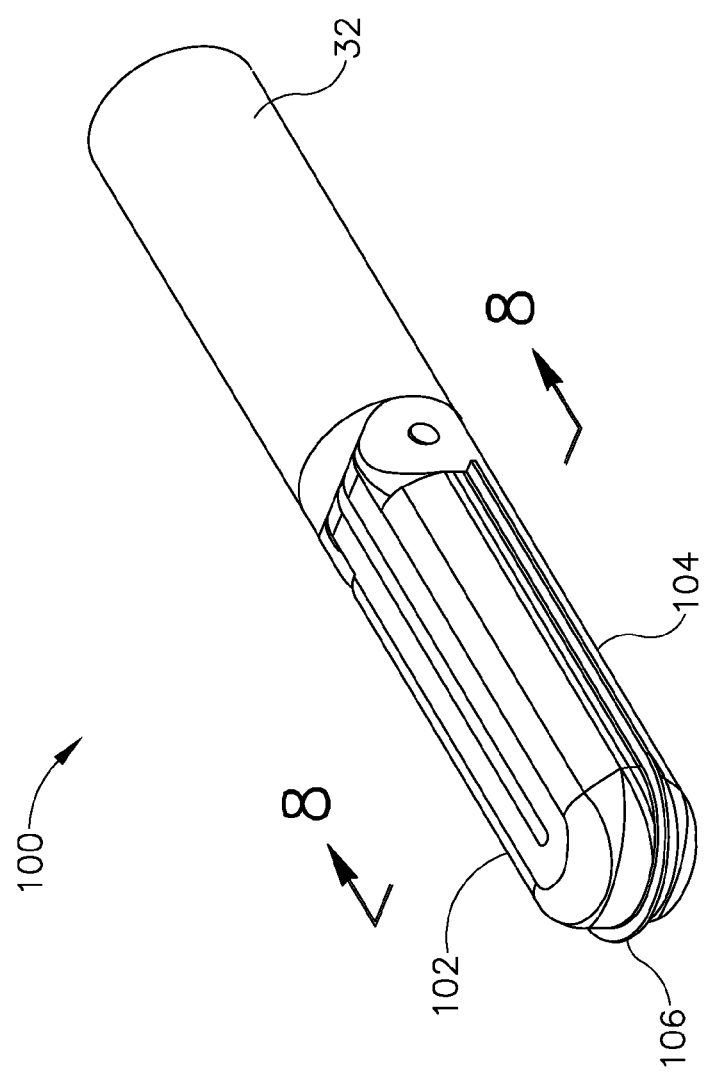
FIG. 6 depicts a perspective view of an exemplary alternative end effector suitable for use in the instrument of FIG. 1, in a closed position.
Figure 7:
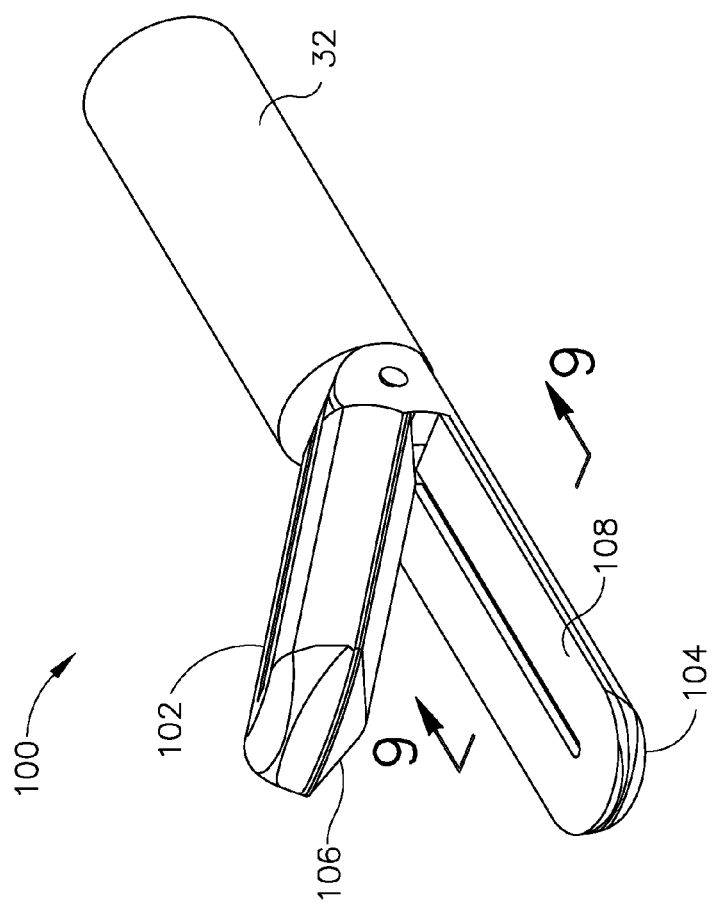
FIG. 7 depicts a perspective view of the end effector of FIG. 6 in an open position.

FIGS. 6 and 7 show an exemplary alternative end effector (100) that may be readily incorporated into instrument (10). End effector (100) comprises an upper jaw (102), a lower jaw (104), an upper electrode (106), a lower electrode (108), and an elastomer (110). End effector (100) is configured to operate substantially similar to end effector (40) discussed above except for the differences discussed below. Upper electrode (106) is coupled to elastomer (110) which is coupled to upper jaw (102). Lower electrode (108) is coupled to lower jaw (104). Upper electrode (106) and lower electrode (108) are positioned such that when upper jaw (102) closes upon lower jaw (104), upper electrode (106) and lower electrode (108) will contact tissue clamped between jaws (102, 104).

Figure 8:
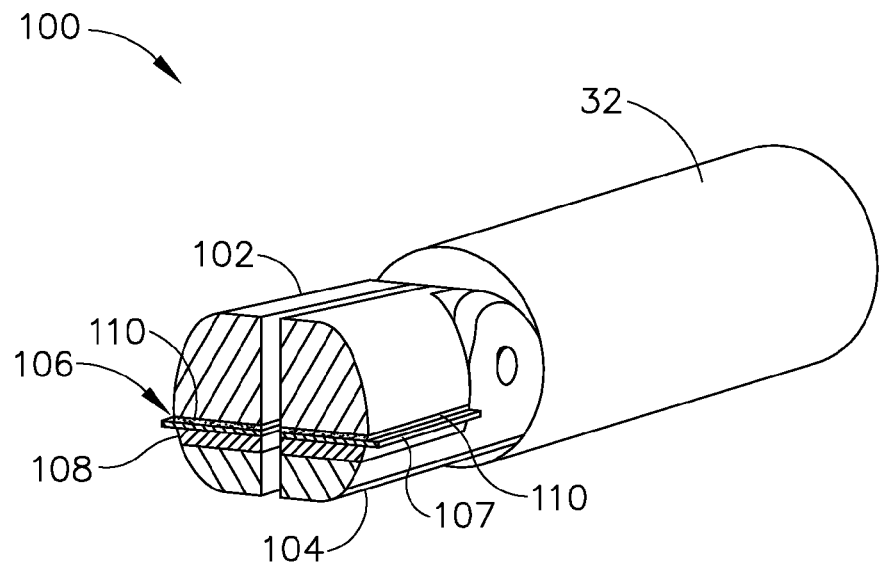
FIG. 8 depicts a cross-sectional perspective view of the end effector of FIG. 6, taken along line 8-8 of FIG. 6.
Figure 13:
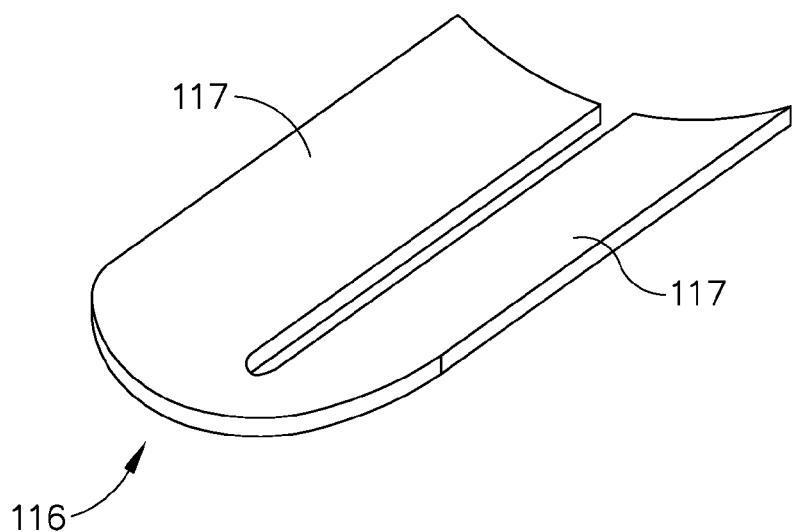
FIG. 13 depicts a front perspective view of an exemplary alternative spring electrode pad.
Figure 14:
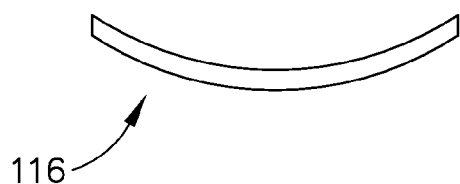
FIG. 14 depicts a front elevational view of the spring electrode pad of FIG. 13.
Figure 15:
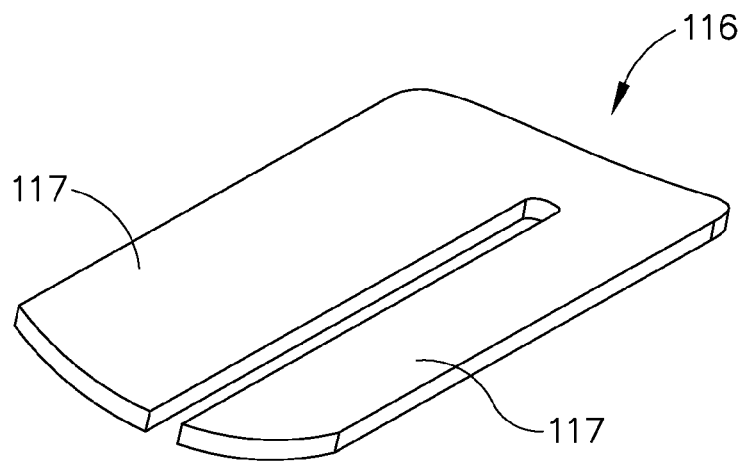
FIG. 15 depicts a rear perspective view of the spring electrode pad of FIG. 13.

As best seen in FIGS. 9-12, upper electrode (106) is resiliently biased to have a generally v-shaped profile such that flanges (107) of upper electrode (106) are inwardly tapered when end effector (100) is in an open position. Although upper electrode (106) of the present example has a v-shaped profile, upper electrode (106) may have other profile. For instance, as shown in FIGS. 13-15, an exemplary alternative upper electrode (116) is resiliently biased to have a curved profile such that flanges (117) of upper electrode (116) are curved when end effector (100) is in an open position. As will be discussed in more detail below, upper electrode (116) may be oriented such that upper electrode forms a convex curve or a concave curve with respect to lower electrode (108). As seen in FIG. 8, when end effector (100) is moved to a closed position, upper electrode (106, 116) is configured to deform to a substantially flat shape due to the forces exerted upon it by closing upper jaw (102) upon lower jaw (104).

Figure 9:
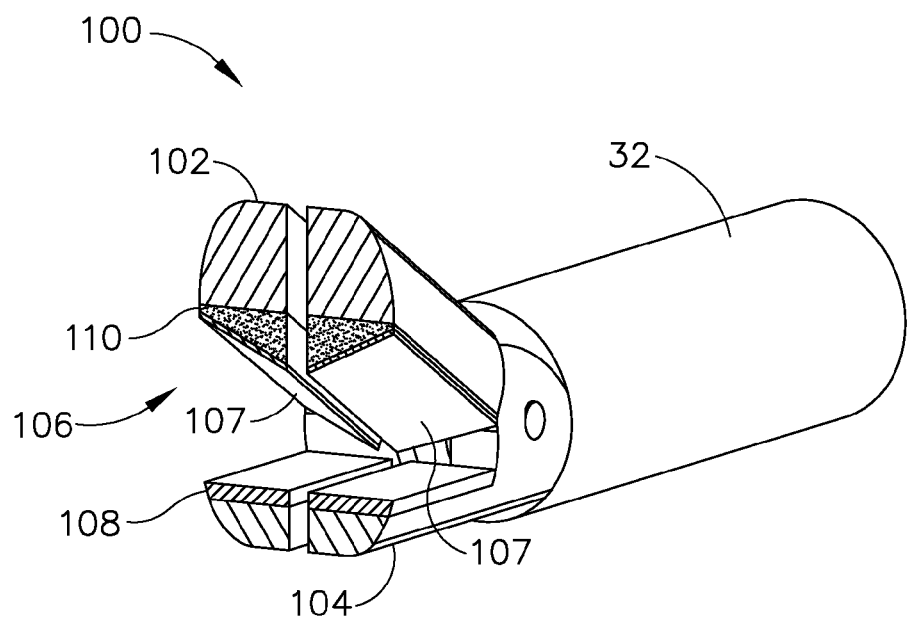
FIG. 9 depicts a cross-sectional perspective view of the end effector of FIG. 6, taken along line 9-9 of FIG. 7.
Figure 10:
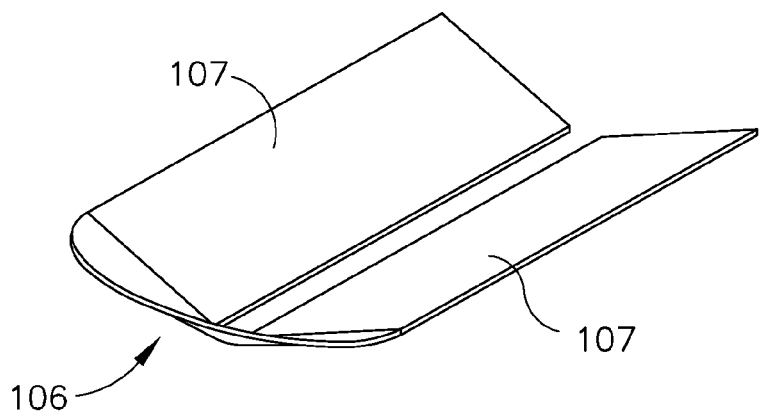
FIG. 10 depicts a front perspective view of an exemplary spring electrode pad.
Figure 11:
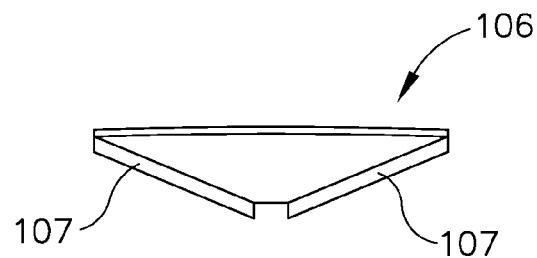
FIG. 11 depicts a front elevational view of the spring electrode pad of FIG. 10.
Figure 12:
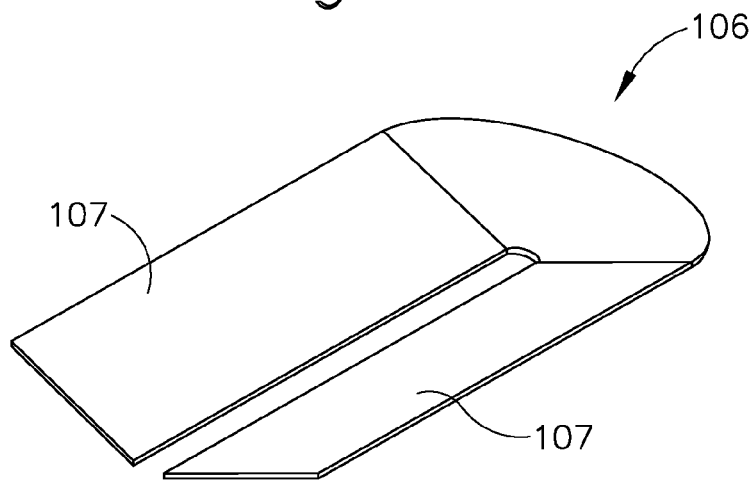
FIG. 12 depicts a rear perspective view of the spring electrode pad of FIG. 10.
Figure 17A:
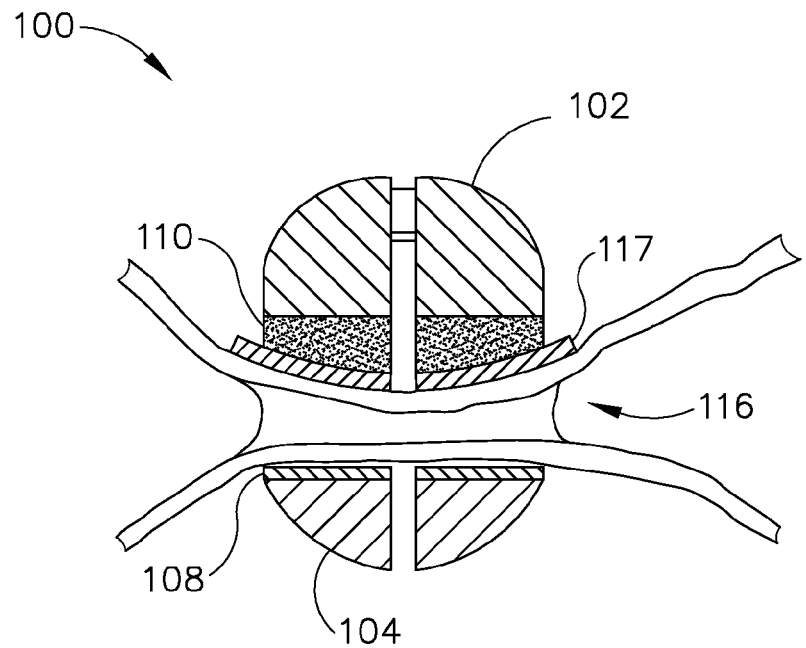
FIG. 17A depicts a cross-sectional view of the end effector of FIG. 6 having the spring electrode pad of FIG. 13 in a convex orientation lightly clamped about tissue, taken along line 9-9 of FIG. 7.
Figure 18A:
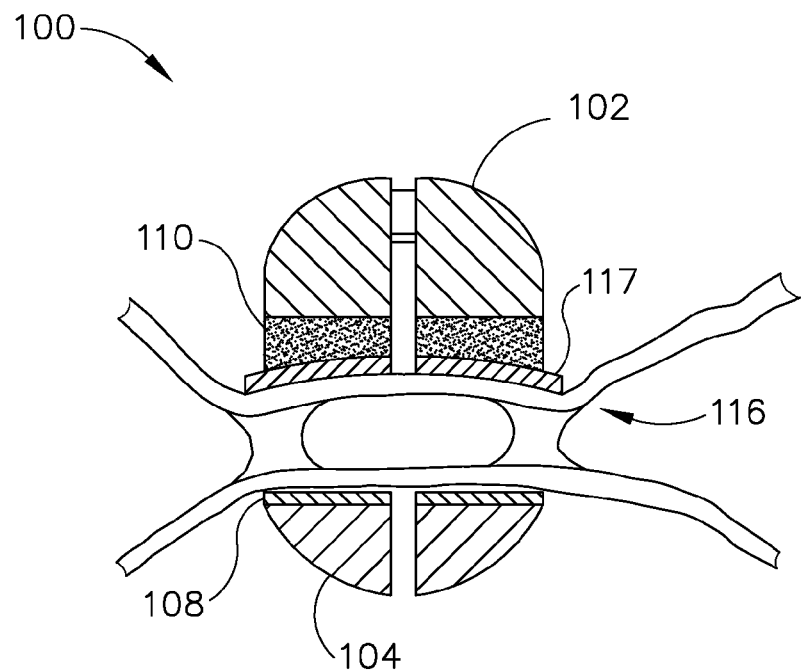
FIG. 18A depicts a cross-sectional view of the end effector of FIG. 6 having the spring electrode pad of FIG. 13 in a concave orientation lightly closed about tissue, taken along line 9-9 of FIG. 7.

As best seen in FIG. 9, the surface of elastomer (110) to which upper electrode (106) is coupled is configured to mirror the shape of upper electrode (106) when end effector (100) is in an open position. Although elastomer (110) of the present example is configured to mirror the shape of upper electrode (106), elastomer (110) may be configured to have any suitable shape. For instance, as shown in FIGS. 17A and 18A, elastomer (110) mirrors the curved profile of upper electrode (116). As seen in FIG. 8, when end effector (100) is moved to a closed position, elastomer (110) is configured to compress and thereby deform with upper electrode (106) due to the forces exerted upon it by closing upper jaw (102) upon lower jaw (104).

A. Exemplary Operation

Figure 16A:
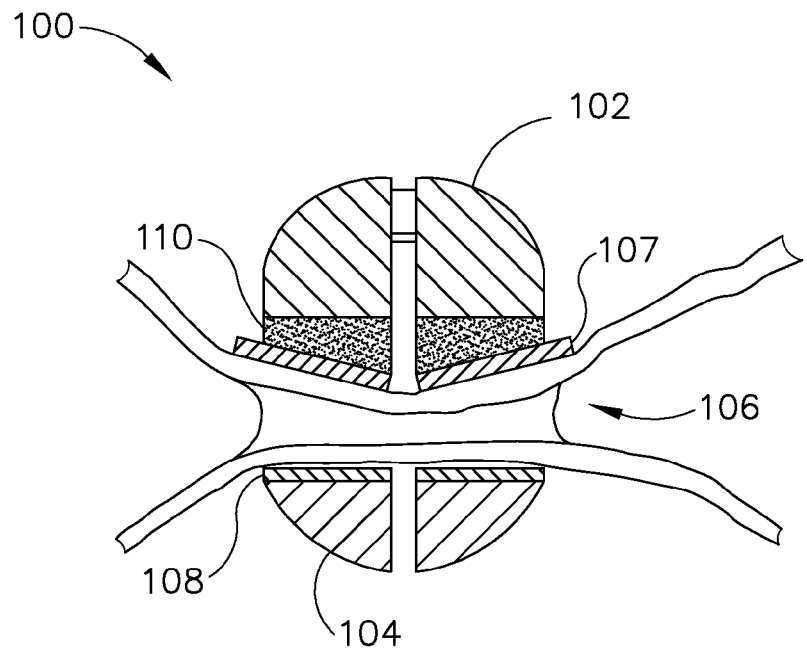
FIG. 16A depicts a cross-sectional view of the end effector of FIG. 6 having the spring electrode pad of FIG. 10 lightly closed about tissue, taken along line 9-9 of FIG. 7.

In an exemplary use, end effector (100) is used to clamp down on tissue such that other operations may be performed by end effector (100) on the tissue while end effector (100) holds the tissue in place. As described above, upper electrode (106) has a v-shaped profile such that flanges (107) of upper electrode (106) are inwardly tapered when end effector (100) is in an open position. In this open position, tissue is received between upper jaw (102) and lower jaw (104) as shown in FIG. 16A. As upper jaw (102) begins to close toward lower jaw (104), a downward force is exerted upon the tissue by upper electrode (106). The taper of flanges (107) causes an initial concentration of this downward force exerted upon the tissue by upper electrode (106) toward the center of upper electrode (106). This initial concentration of the downward force exerted upon the tissue by upper electrode (106) may cause the tissue to be squeezed outwardly.

Figure 16B:
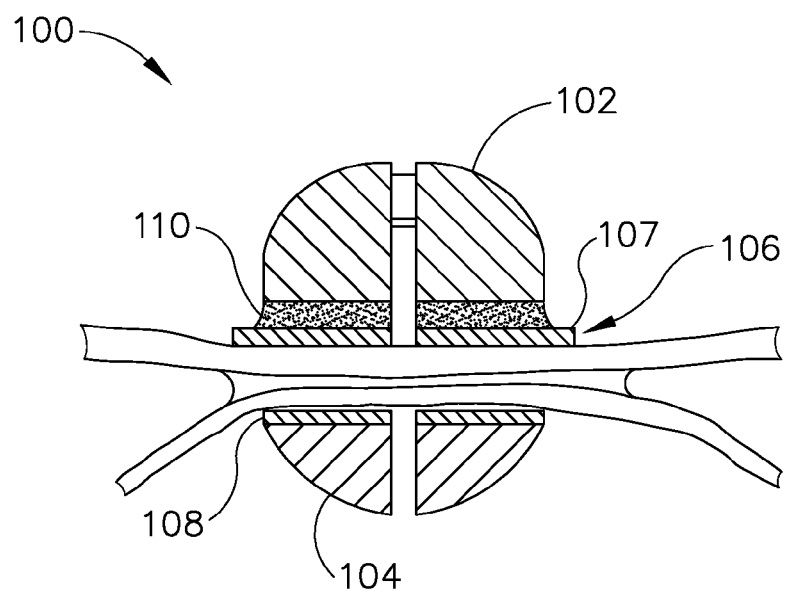
FIG. 16B depicts a cross-sectional view of the end effector of FIG. 6 having the spring electrode pad of FIG. 10 fully clamped about tissue, taken along line 8-8 of FIG. 6.

As upper jaw (102) is moved closer toward lower jaw (104), the tissue increasingly exerts an upward force upon upper electrode (106). The force exerted upon upper electrode (106) by the tissue causes upper electrode (106) and the elasomer (110) to begin to deform. As discussed above, once end effector (100) is moved to the closed position, upper electrode (106) will have deformed to a substantially flat shape due to the forces exerted upon it by the tissue. As seen in FIG. 16B, during this process of closing upper jaw (102) toward lower jaw (104), upper electrode (106) will deform from an initial tapered configuration—where the forces exerted upon the tissue by upper electrode (106) are concentrated toward the center of upper electrode (106)—to a substantially flat configuration—where the forces exerted upon the tissue by upper electrode (106) are spread more evenly across the surface area of upper electrode (106). Therefore, it should be understood that the force exerted upon the tissue by upper electrode (106) transitions outwardly across the surface of upper electrode (106) from an initial central concentration to a more even distribution across upper electrode (106). This outward transition of force may cause the fluids in the tissue to likewise transition outwardly such that tissue is all that remains between upper jaw (102) and lower jaw (104) when jaws (102, 104) are fully clamped.

In settings where the tissue clamped between jaws (102, 104) includes muscle, the transitioning clamping action of electrode (106) may aid in fracturing muscle within the tissue and driving the muscle outwardly relative to the clamping area between jaws (102, 104). The transitioning clamping action of electrode (106) may also substantially prevent movement of the tissue relative to jaws (102, 104), as compared to configurations where electrodes are simply flat or have other characteristics. Furthermore, by providing greater localization of the effective clamping surface area at any given instant during the clamping process (at least until jaws (102, 104) are fully clamped), the configuration of electrode (106) may also reduce the force required to close jaws (102, 104).

Once end effector (100) has been moved to the closed position the tissue will be firmly clamped and the user may operate upon the tissue as discussed in relation to end effector (40) above. By way of example only, the user may activate electrodes (106, 108) to seal the tissue and drive firing beam (60) through the tissue to sever the tissue.

B. Exemplary Alternative Operation

As described above, upper electrode (116) shown in FIGS. 10-12 has a curved profile such that flanges (117) of upper electrode (116) are curved when end effector (100) is in an open position. In this open position, tissue is received between upper jaw (102) and lower jaw (104) as shown in FIG. 17A. In the present example, upper electrode (116) is oriented such that upper electrode (116) forms a convex curve with respect to lower electrode (108). As upper jaw (102) begins to close toward lower jaw (104), a downward force is exerted upon the tissue by upper electrode (116). The curve of flanges (117) causes an initial concentration of this downward force exerted upon the tissue by upper electrode (116) toward the center of upper electrode (116). This initial concentration of the downward force exerted upon the tissue by upper electrode (116) may cause the tissue to be squeezed outwardly.

Figure 17B:
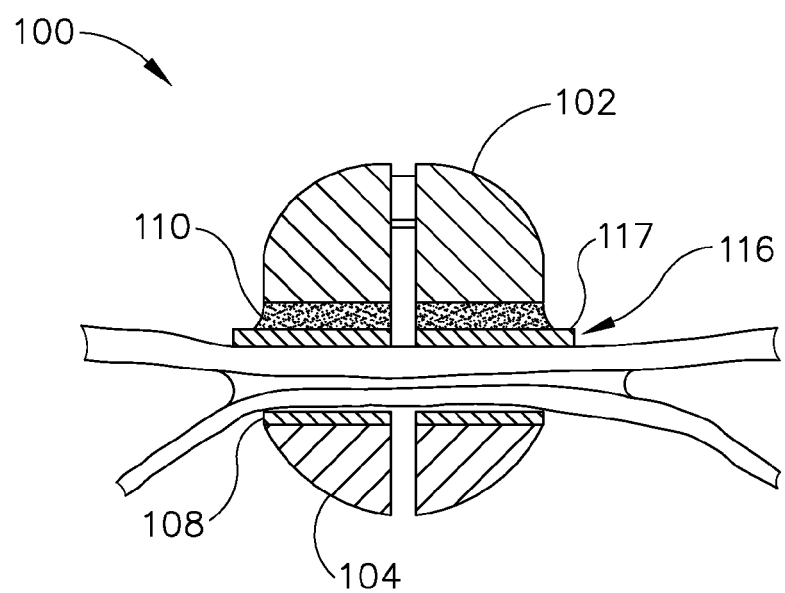
FIG. 17B depicts a cross-sectional view of the end effector of FIG. 6 having the spring electrode pad of FIG. 13 in a flat orientation fully clamped about tissue, taken along line 8-8 of FIG. 6.

As upper jaw (102) is moved closer toward lower jaw (104), the tissue increasingly exerts an upward force upon upper electrode (116). The force exerted upon upper electrode (116) by the tissue causes upper electrode (116) and elastomer (110) to begin to deform. As shown in FIG. 17B, once end effector (100) is moved to the filly closed position, upper electrode (116) will have deformed to a substantially flat shape due to the forces exerted upon it by the tissue. During this process of closing upper jaw (102) toward lower jaw (104), upper electrode (116) will deform from an initial curved configuration—where the forces exerted upon the tissue by upper electrode (116) are concentrated toward the center of upper electrode (116)—to a substantially flat configuration—where the forces exerted upon the tissue by upper electrode (116) are spread across the surface area of upper electrode (116). Therefore, it should be understood that the force exerted upon the tissue by upper electrode (116) transitions outwardly across the surface of upper electrode (116) from an initial central concentration to a more even distribution across upper electrode (116). This outward transition of force may cause any fluid within the tissue to likewise transition outwardly such that tissue is all that remains between upper jaw (102) and lower jaw (104) when jaws (102, 104) are fully clamped.

In settings where the tissue clamped between jaws (102, 104) includes muscle, the transitioning clamping action of electrode (116) may aid in fracturing muscle within the tissue and driving the muscle outwardly relative to the clamping area between jaws (102, 104). The transitioning clamping action of electrode (116) may also substantially prevent movement of the tissue relative to jaws (102, 104), as compared to configurations where electrodes are simply flat or have other characteristics. Furthermore, by providing greater localization of the effective clamping surface area at any given instant during the clamping process (at least until jaws (102, 104) are fully clamped), the configuration of electrode (116) may also reduce the force required to close jaws (102, 104).

As shown in FIG. 18A, upper electrode (116) may be alternatively oriented such that upper electrode forms a concave curve with respect to lower electrode (108). Elastomer (110) may again complement this curvature. In this open position, tissue is received between upper jaw (102) and lower jaw (104) as shown in FIG. 18A. As upper jaw (102) begins to close toward lower jaw (104), a downward force is exerted upon the tissue by upper electrode (116). The curve of flanges (117) causes an initial concentration of the downward force exerted upon the tissue by upper electrode (116) toward the outer edges of upper electrode (116). This initial concentration of the downward force exerted upon the tissue by upper electrode (116) may cause the tissue to be squeezed inwardly such that upper electrode (116) is clamped most firmly on tissue along the outer edge of upper electrode.

Figure 18B:
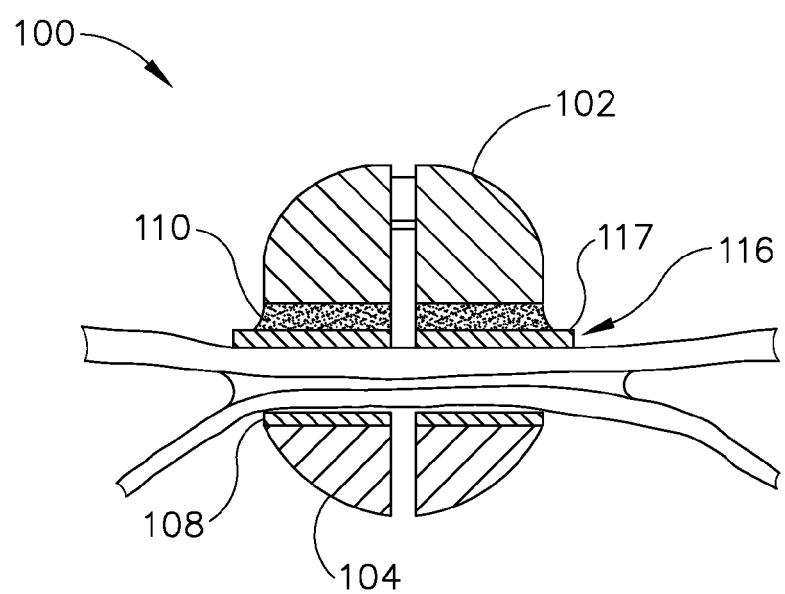
FIG. 18B depicts a cross-sectional view of the end effector of FIG. 6 having the spring electrode pad of FIG. 13 in a flat orientation fully clamped about tissue, taken along line 8-8 of FIG. 6.

As upper jaw (102) is moved closer toward lower jaw (104), the tissue increasingly exerts an upward force upon upper electrode (116). The force exerted upon upper electrode (116) by the tissue causes upper electrode (116) and elastomer (110) to begin to deform. As shown in FIG. 18B, once end effector (100) is moved to the closed position, upper electrode (116) will have deformed to a substantially flat shape due to the forces exerted upon it by the tissue. During this process of closing upper jaw (102) toward lower jaw (104), the outer edge of upper electrode (116) will move in an outward direction, taking with it the clamped tissue regions. Therefore, it should be understood, that moving end effector (100) into the closed position will cause the tissue that is initially clamped within the outer edges of the upper electrode (116) to be pulled in an outward direction. This pulling may cause fluid within the tissue to be squeezed out such that tissue is all that remains between upper jaw (102) and lower jaw (104).

In settings where the tissue clamped between jaws (102, 104) includes muscle, the transitioning clamping action of electrode (116) may aid in fracturing muscle within the tissue. The transitioning clamping action of electrode (116)

may also substantially prevent movement of the tissue relative to jaws (102, 104), as compared to configurations where electrodes are simply flat or have other characteristics. Furthermore, by providing greater localization of the effective clamping surface area at any given instant during the clamping process (at least until jaws (102, 104) are fully clamped), the configuration of electrode (116) may also reduce the force required to close jaws (102, 104).

Once end effector (100) has been moved to the closed position the tissue will be firmly clamped and the user may operate upon the tissue as discussed in relation to end effector (40) discussed above. By way of example only, the user may activate electrodes (106, 108) to seal the tissue and drive firing beam (60) through the tissue to sever the tissue.

While shaped electrodes (106, 116) and elastomer (110) are shown as being part of upper jaw (102), it should be understood that lower jaw (104) may incorporate shaped electrodes (106, 116) and elastomer (110) in addition to or in lieu of upper jaw incorporating electrodes (106, 116) and elastomer (110).

III. Exemplary Alternative End Effector

Figure 19:
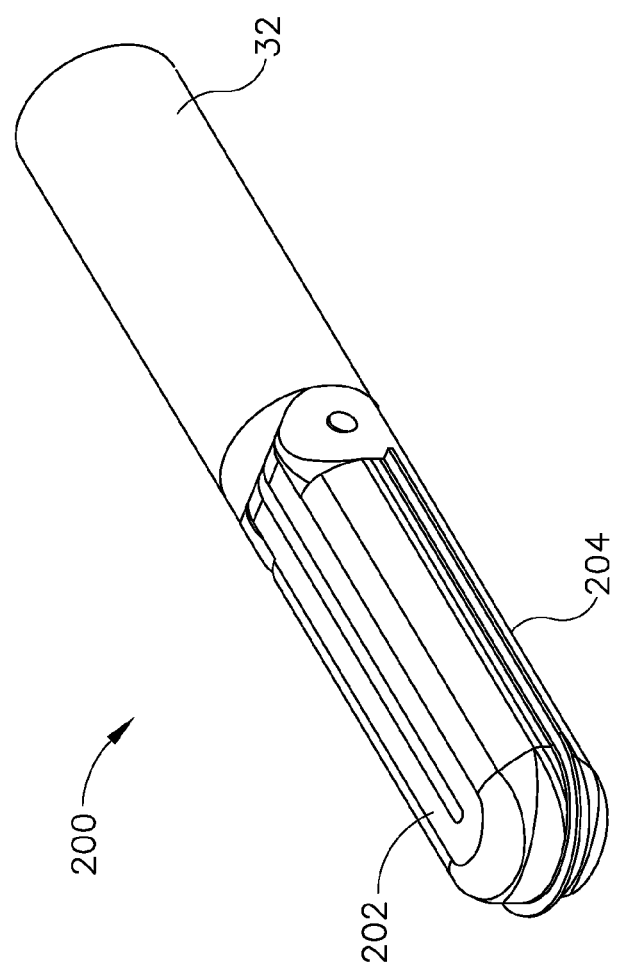
FIG. 19 depicts a perspective view of another exemplary alternative end effector in a closed position.
Figure 20:
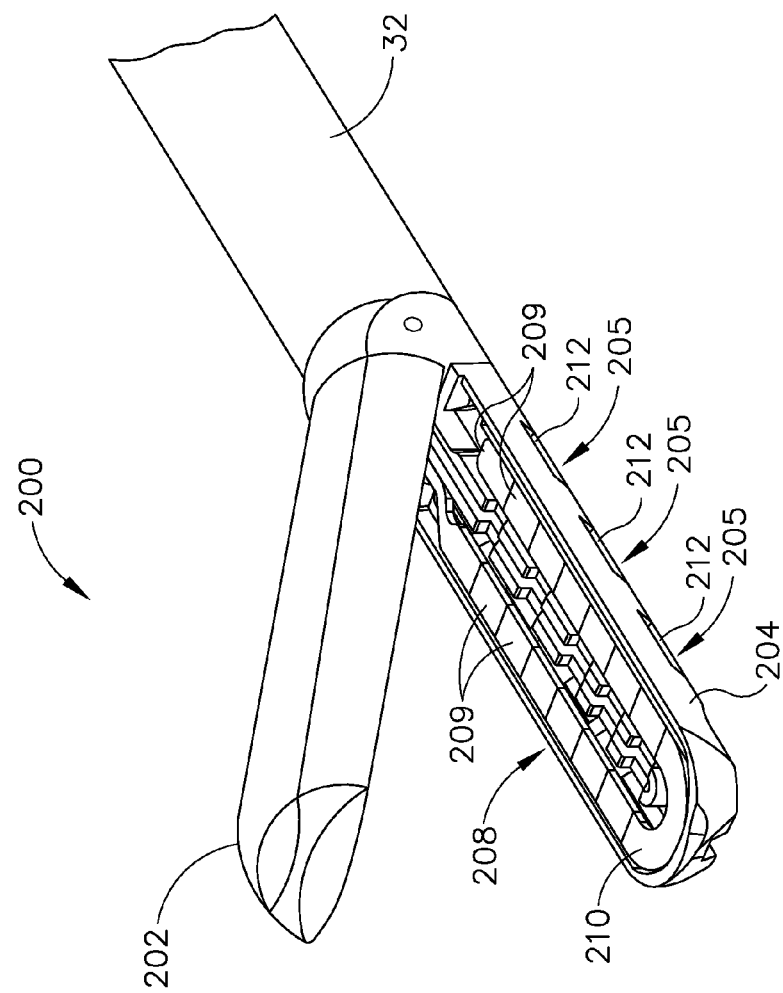
FIG. 20 depicts a perspective view of the end effector of FIG. 19 in an open position.

FIGS. 19 and 20 show another exemplary alternative end effector (200) that may be readily incorporated into instrument (10). It should be understood that end effector (200) may be used to clamp, seal, and sever tissue just like end effector (40) discussed above. End effector (200) comprises an upper jaw (202), a lower jaw (204), an upper electrode (not shown), a lower electrode (208), and an elastomer (210). End effector (200) is configured to operate substantially similar to end effector (40) discussed above except for the differences discussed below. Upper electrode is coupled to the underside of upper jaw (202). Lower electrode (208) is coupled to elastomer (210), which is disposed within lower jaw (204). Among other coupling methods, lower electrode (208) may be insert-molded within elastomer (210). Upper electrode and lower electrode (208) are positioned such that when upper jaw (202) closes upon lower jaw (204), upper electrode and lower electrode (208) will contact tissue captured between jaws (204). Elastomer (210) is an insulator and thus provides electrical isolation of electrode (208) relative to the remainder of lower jaw (204). By way of example only, elastomer (210) may comprise a peroxide cured high temperature elastomer.

Figure 21:
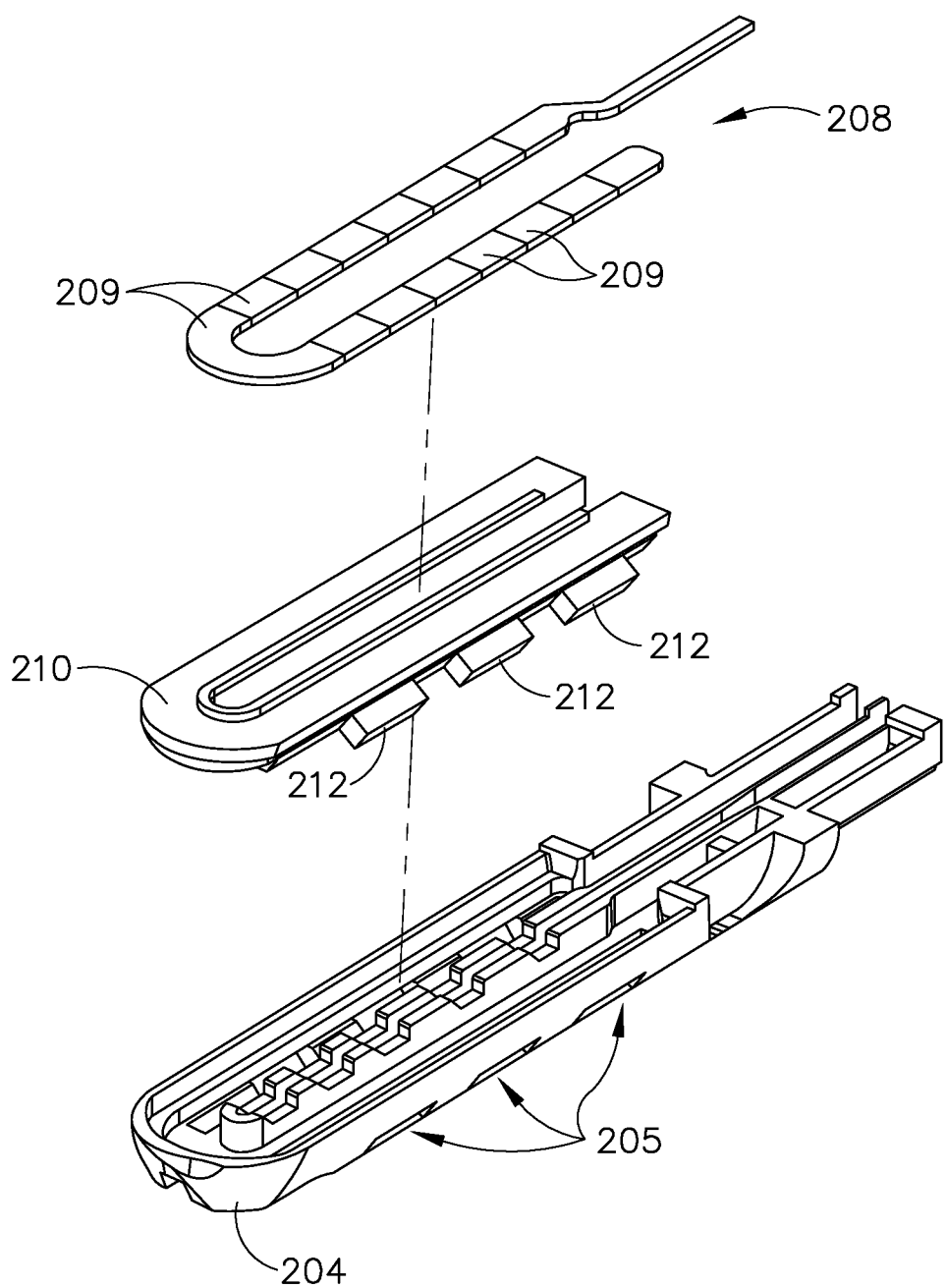
FIG. 21 depicts an exploded perspective view of the lower jaw of the end effector of FIG. 19.

As shown in FIG. 21, lower electrode (208) comprises a series of segments (209).

Segments (209) are coupled together such that energy may be communicated between segments (209). However, segments (209) are configured to allow lower electrode (208) to deform in response to variable pressures exerted upon lower electrode (208) during operation. For instance, variable pressures may be applied to lower electrode (208) due to variable tissue thicknesses/densities. In some versions, segments (209) are joined by living hinges. In some other versions, segments (209) are secured to a flexible conductive substrate. Elastomer (210), to which lower electrode (208) is coupled, is also flexible. Therefore, elastomer (210) may also deform in response to variable pressures exerted upon lower electrode (208) during operation. As best seen in FIG. 21, lower jaw (204) comprises a series of slots (205) that receive corresponding protrusions (212) of elastomer (210) to thereby secure elastomer (210) to lower jaw (204). Slots (205) also allow for protrusions (212) to slide inwardly and outwardly within slots (205). For instance, as tissue is compressed between jaws (202, 204), elastomer (210) may compress such that protrusions (212) are driven outwardly through slots (205). When the tissue is released, elastomer may resiliently deform back to its initial state such that protrusions (212) recede back inwardly through slots (205).

IV. Exemplary Alternative End Effector

Figure 22:
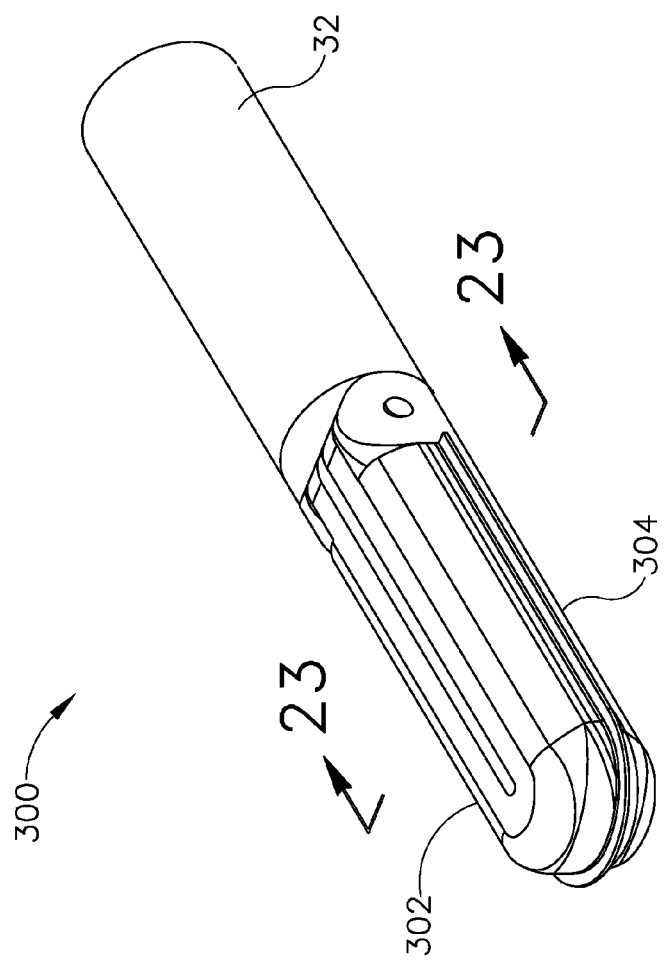
FIG. 22 depicts a perspective view of another exemplary alternative end effector in a closed position.

FIG. 22 shows another exemplary alternative end effector (300) that may be readily incorporated into instrument (10). It should be understood that end effector (300) may be used to clamp, seal, and sever tissue just like end effector (40) discussed above. End effector (300) comprises an upper jaw (302), a lower jaw (304), an upper electrode (306), a lower electrode (308), an insulator (310), and a resilient member (312). End effector (300) is configured to operate substantially similar to end effector (40) discussed above except for the differences discussed below. Upper electrode (306) is coupled to upper jaw (302). Lower electrode (308) is coupled to insulator (310), which rests upon resilient member (312) such that lower electrode (308) effectively floats relative to lower jaw (304). Insulator (310) comprises a plurality of guides (311) that are slidably disposed within lower jaw (304). Resilient member (312) comprises an elastomeric rod-shaped member that extends along the length of lower jaw (304) in this example, though it should be understood that flexible member may take any other suitable form. Insulator (310) is configured to move downwardly as shown in FIG. 23B by compressing resilient member (312) in response to pressure from upper jaw (302) as end effector (300) is closed upon tissue. Guides (311) of insulator (310) guide insulator (310) during this vertical movement, preventing lateral and longitudinal movement of insulator (310) relative to lower jaw (304) while permitting vertical movement of insulator (310) relative to lower jaw (304). Upper electrode (306) and lower electrode (308) are positioned such that when upper jaw (302) closes upon lower jaw (304), upper electrode (306) and lower electrode (308) will contact tissue that is captured between jaws (302, 304).

Figure 23A:
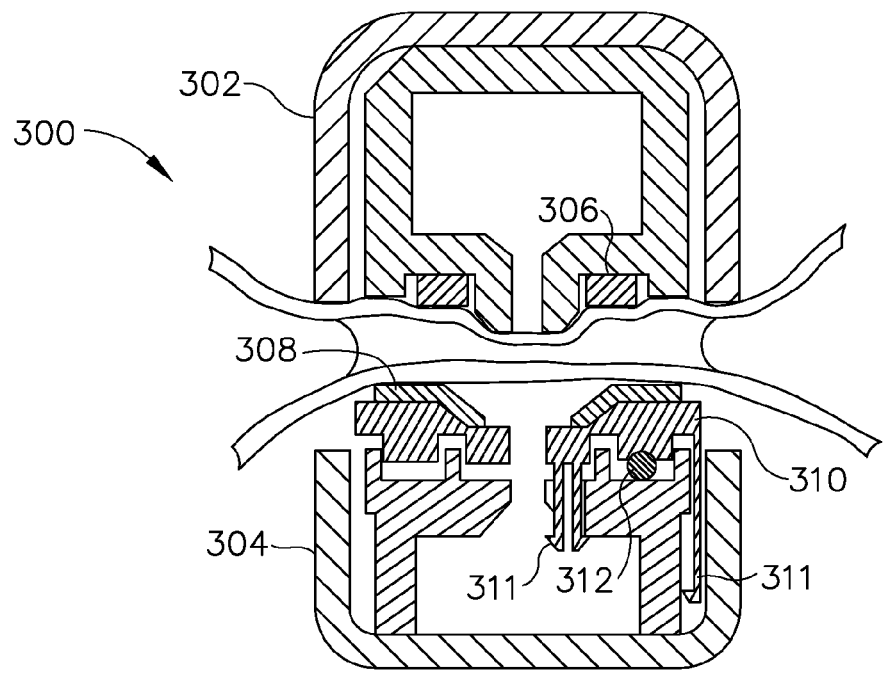
FIG. 23A depicts a cross-sectional view of the end effector of FIG. 22 having an exemplary insulator lightly closed about tissue, taken along line 23-23 of FIG. 22.
Figure 23B:
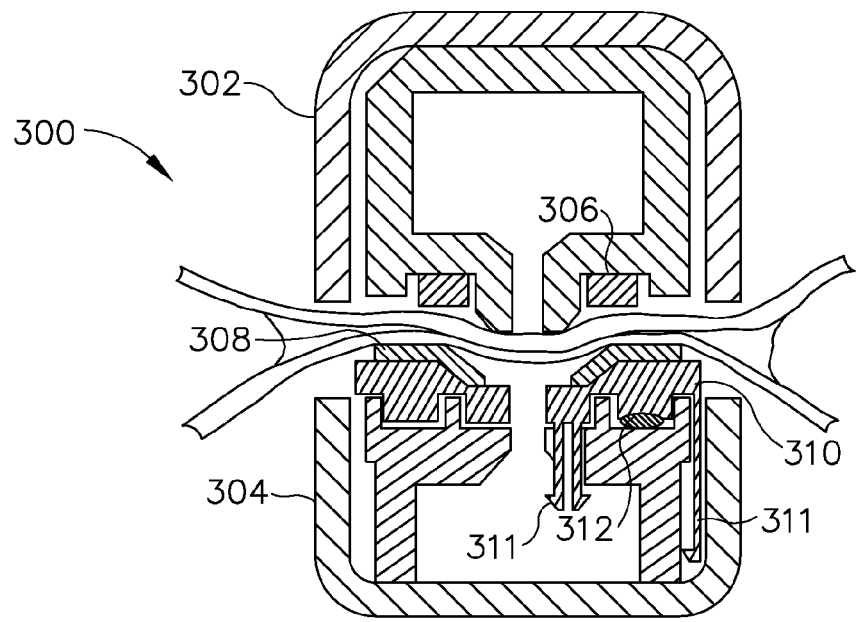
FIG. 23B depicts a cross-sectional view of the end effector of FIG. 22 having the insulator of FIG. 23A fully clamped about tissue, taken along line 23-23 of FIG. 22.

In an open position, tissue is received between upper jaw (302) and lower jaw (304) as shown in FIG. 23A. In the open position, resilient member (312) is not compressed and insulator (310) remains in an upward position. As upper jaw (302) is closed upon the tissue, the downward force exerted upon insulator (310) from upper jaw (302) forces resilient member (312) to compress and insulator (310) is moved to a downward position as shown in FIG. 23B. It should be understood that as resilient member (312) is compressed it exerts an increasing amount of resistance pressure against the downward force imposed upon it by upper jaw (302). Thus is should likewise be understood that in the open position the force exerted upon insulator (310) is at a minimum and in the closed position the force exerted upon insulator (310) has steadily increased to a maximum.

Figure 24A:
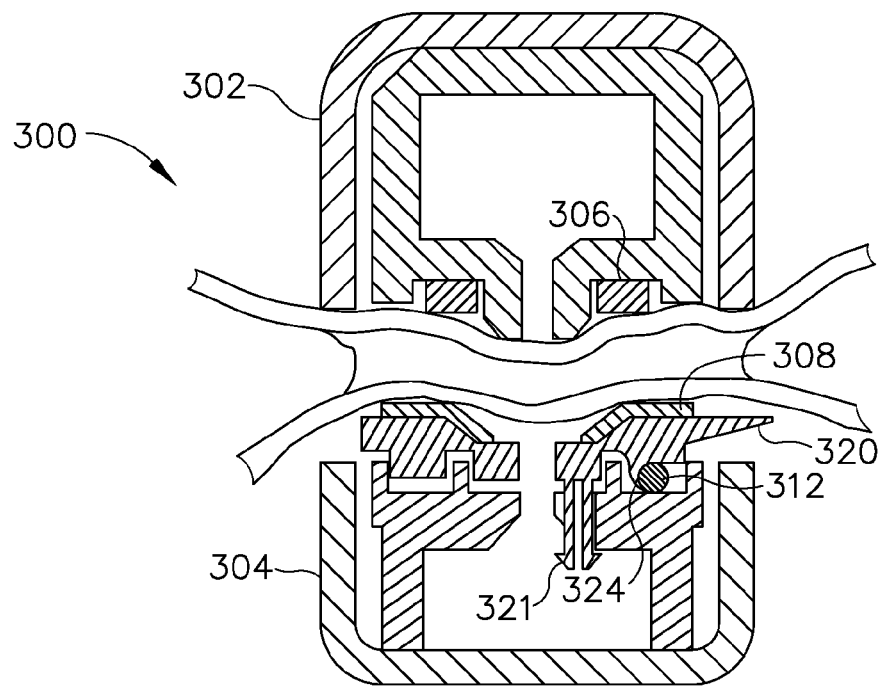
FIG. 24A depicts a cross-sectional view of the end effector of FIG. 22 having another exemplary insulator lightly closed about tissue, taken along line 23-23 of FIG. 22.
Figure 24B:
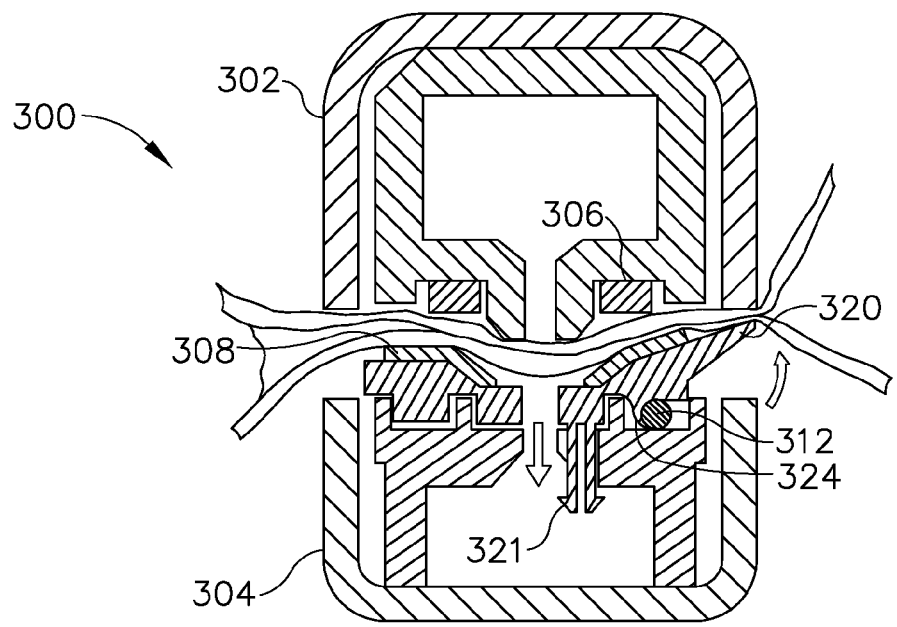
FIG. 24B depicts a cross-sectional view of the end effector of FIG. 22 having the insulator of FIG. 24A fully clamped about tissue, taken along line 23-23 of FIG. 22.

Although insulator (310) of the present example is configured to move downwardly in response to pressure from upper jaw (302), insulator 9310) may be configured to respond differently to such pressure. For instance, as shown in FIGS. 24A-24B, an insulator (320) comprises a pivot member (324). When tissue is compressed between jaws (302, 304) in this example, resilient member (312) applies an inward and upward force to insulator (320) and electrode (308). In addition, pivot member (324) causes insulator (320) and electrode (308) to rotate in a counter-clockwise manner in response to the downward force from upper jaw (302). As insulator (320) moves in a counter-clockwise direction, force is applied to the tissue inwardly and upwardly. It should be understood that this clamping action may aid in fracturing any muscle within the tissue clamped between jaws (302, 304), aid in retaining tissue within jaws (302, 304) for grasping, and/or provide other results as described herein.

V. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010; now U.S. Pat. No. 8,408,439, issued on Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S.

Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an upper jaw;
   (b) a lower jaw, wherein the upper jaw and the lower jaw are configured to receive tissue when in an open position, and wherein the upper jaw is movable toward the lower jaw from the open position to a closed position;
   (c) a flexible member comprising a first face and a second face, wherein the first face of the flexible member is coupled to one of either the upper jaw or the lower jaw, wherein the first face and the second face define an oblique angle while the upper jaw and the lower jaw are in the open position, wherein the first face and the second face are deformable to be parallel with each other when the upper jaw and the lower jaw are in the closed position; and
   (d) a pair of conductive members, wherein a first conductive member of the pair of conductive members is associated with the upper jaw, wherein a second conductive member of the pair of conductive members is associated with the lower jaw, wherein the flexible member is configured to deform in response to compression of tissue between the pair of conductive members, and wherein the conductive members are configured to communicate energy to tissue;
   wherein one or both of the first conductive member or the second conductive member comprises a plurality of segments.

2. The apparatus of claim 1, wherein either the first conductive member or the second conductive member is coupled to the flexible member.

3. The apparatus of claim 1, wherein the first conductive member is configured such that a central portion of the first conductive member is positioned to contact tissue between the upper jaw and the lower jaw prior to the rest of the first conductive member.

4. The apparatus of claim 3, wherein the first conductive member has an inwardly tapered profile.

5. The apparatus of claim 3, wherein the first conductive member has a curved profile.

6. The apparatus of claim 1, wherein the first conductive member is configured such that an outer edge of the conductive member contacts tissue between the upper jaw and the lower jaw prior to the rest of the first conductive member.

7. The apparatus of claim 6, wherein the first conductive member has a curved profile.

8. The apparatus of claim 1, wherein the lower jaw presents a plurality of openings, and wherein the flexible member is configured to move within the openings in response to compression of tissue between the pair of conductive members.

9. The apparatus of claim 8, wherein the flexible member comprises a plurality of tabs, and wherein the tabs are disposed within the openings of the lower jaw.

10. The apparatus of claim 1, further comprising an insulator, wherein the second conductive member is coupled to the insulator.

11. The apparatus of claim 10, wherein the insulator comprises a plurality of guides, wherein the guides are slidably disposed within the lower jaw, and wherein the flexible member is between the insulator and the lower jaw.

12. The apparatus of claim 11, wherein the insulator is configured to move in a downward direction in response to compression of tissue between the pair of conductive members.

13. The apparatus of claim 11, wherein the insulator is configured to rotate about a pivot member of the insulator in response to compression of tissue between the pair of conductive members.

14. The apparatus of claim 1, wherein the pair of conductive members, and the flexible member are configured to drive tissue in an outward direction in response to compression of tissue between the pair of conductive members.

15. The apparatus of claim 1, wherein the pair of conductive members and the flexible member are configured to stretch tissue in an outward direction in response to compression of tissue between the pair of conductive members.

16. An apparatus for operating on tissue, the apparatus comprising:
 (a) an upper jaw,
 (b) a lower jaw, wherein the upper jaw and the lower jaw are configured to receive tissue when in an open position, and wherein the upper jaw is movable toward the lower jaw from the open position to a closed position;
 (c) a flexible member comprising a first face and a second face, wherein the first face of the flexible member is coupled to one of either the upper jaw or the lower jaw, wherein the first face and the second face define an oblique angle while the upper jaw and the lower jaw are in the open position, wherein the first face and the second face are deformable to be parallel with each other when the upper jaw and the lower jaw are in the closed position; and
 (d) a pair of conductive members, wherein a first conductive member of the pair of conductive members is associated with the upper jaw, wherein a second conductive member of the pair of conductive members is associated with the lower jaw, wherein the flexible member is configured to deform in response to compression of tissue between the pair of conductive members, and wherein the conductive members are configured to communicate energy to tissue;
 wherein the lower jaw presents a plurality of openings, and wherein the flexible member is configured to move within the openings in response to compression of tissue between the pair of conductive members.

\* \* \* \* \*